United States Patent
Yao et al.

(10) Patent No.: US 9,410,120 B2
(45) Date of Patent: Aug. 9, 2016

(54) COMPOSITION FOR EMBRYO CULTURE

(75) Inventors: Tatsuma Yao, Osaka (JP); Yuta Asayama, Osaka (JP); Akio Matsuhisa, Osaka (JP)

(73) Assignee: FUSO PHARMACEUTICAL INDUSTRIES, LTD., Osaka (JP)

( * ) Notice: Subject to any disclaimer, the term of this patent is extended or adjusted under 35 U.S.C. 154(b) by 0 days.

(21) Appl. No.: 14/236,534

(22) PCT Filed: Jul. 18, 2012

(86) PCT No.: PCT/JP2012/068212
§ 371 (c)(1),
(2), (4) Date: Jan. 31, 2014

(87) PCT Pub. No.: WO2013/018545
PCT Pub. Date: Feb. 7, 2013

(65) Prior Publication Data
US 2014/0206082 A1    Jul. 24, 2014

(30) Foreign Application Priority Data
Aug. 3, 2011   (JP) .................. 2011-169910

(51) Int. Cl.
*C12N 5/00* (2006.01)
*C12N 1/00* (2006.01)
*C12N 5/073* (2010.01)

(52) U.S. Cl.
CPC .......... *C12N 5/0604* (2013.01); *C12N 2500/32* (2013.01)

(58) Field of Classification Search
CPC ................. C12N 5/00; C12N 1/00
See application file for complete search history.

(56) References Cited

U.S. PATENT DOCUMENTS

| | | | |
|---|---|---|---|
| 6,130,086 A * | 10/2000 | Nakazawa et al. | 435/325 |
| 2003/0091972 A1 | 5/2003 | Gardner et al. | |
| 2005/0064589 A1* | 3/2005 | Kaplan | C12N 5/0604 435/366 |
| 2005/0239040 A1* | 10/2005 | Lindenberg | C12M 21/06 435/2 |
| 2009/0226879 A1 | 9/2009 | Abdullah | |
| 2013/0309708 A1* | 11/2013 | Robins et al. | 435/29 |

FOREIGN PATENT DOCUMENTS

| JP | 2003-24055 | 1/2003 |
|---|---|---|
| JP | 2003-517276 | 5/2003 |
| JP | 2005-261252 | 9/2005 |

OTHER PUBLICATIONS

Takenaka et al. *PNAS*, vol. 104. No. 36, pp. 14289-14293 (2007).
*Manipulating the Mouse Embryo*, Third Edition, pp. 149-193 (2005).
Rinaudo et al. *Fertility and Sterility*, vol. 86, Supplement 3, pp. 1252-1265 (2006).
Erbach et al. *Biology of Reproduction*, vol. 5, pp. 1027-1033 (1994).
Fernandez-Gonzalez et al. *Reproduction*, vol. 137, pp. 271-283 (2009).
Gardner et al. *Seminars in Reproductive Medicine*, vol. 18, No. 2, pp. 205-218 (2000).
Ho et al. *Molecular Reproduction and Development*, vol. 41, pp. 232-238 (1995).
Quinn et al. *Human Reproduction*, vol. 13, Supplement 4, pp. 173-183 (1998).
Summers et al. *Human Reproduction Update*, vol. 9, No. 6, pp. 557-582 (2003).
Devreker et al. *Human Reproduction*, vol. 16, No. 4, pp. 749-756 (2001).
Baltz. "Media composition: salts and osmolality". Methods in Molecular Biology, Humana Press, Inc., vol. 912, No. 1, pp. 61-80, 2012.

* cited by examiner

*Primary Examiner* — Karen Cochrane Carlson
*Assistant Examiner* — Natalie Moss
(74) *Attorney, Agent, or Firm* — Hamre, Schumann, Mueller & Larson, P.C.

(57) ABSTRACT

Provided is a composition for embryo culture, which contains a constitution suitable for embryo culture. Provided is a composition for embryo culture, which contains (a) a constitution shown in Table A below.

TABLE A

| Components | mM |
|---|---|
| L-Alanine | 0.297 ± 0.089 |
| L-Asparagine | 0.015 ± 0.005 |
| L-Aspartic acid | 0.120 ± 0.036 |
| L-Glutamic acid | 0.550 ± 0.165 |
| Glycine | 0.979 ± 0.294 |
| L(−)-Proline | 0.105 ± 0.032 |
| L-Serine | 0.176 ± 0.053 |
| L(+)-Arginine | 0.108 ± 0.032 |
| L(−)-Cystine | 0.048 ± 0.014 |
| L-Histidine | 0.053 ± 0.016 |
| L(+)-Isoleucine | 0.036 ± 0.011 |
| L-Leucine | 0.081 ± 0.024 |
| L(+)-Lysine | 0.176 ± 0.053 |
| L-Methionine | 0.022 ± 0.007 |
| L(−)-Phenylalanine | 0.045 ± 0.013 |
| L(−)-Threonine | 0.109 ± 0.033 |
| L-Tryptophan | 0.018 ± 0.005 |
| L-Tyrosine | 0.048 ± 0.014 |
| L-Valine | 0.108 ± 0.032 |
| L-Glutamine or glutamine derivative | 0.398 ± 0.119 |
| Taurine | 1.412 ± 0.424 |

7 Claims, No Drawings

COMPOSITION FOR EMBRYO CULTURE

TECHNICAL FIELD

The present invention relates to a culture composition. More particularly, the present invention relates to a composition for embryo culture.

BACKGROUND ART

In vitro fertilization, embryo culture and embryo transplantation and the like are important techniques in a wide range of fields such as the improvement and production of animals with a high economic value, regenerative medicine and reproductive medicine. In in vitro fertilization and embryo culture, gametes or embryos are treated in vitro. Until now, various media for embryo culture have been developed, such as sequential culture media which are made to imitate changes in the environment of peripheral body fluids during embryonic development, serum media which are supplemented with serum and serum-free simple media called "single medium" which can be easily treated. When using a single medium, medium exchange in accordance with the developmental stage of embryos as a sequential culture media is not required. When using a serum-free medium, risks which are caused in serum media can be reduced, such as quality variation, and virus contamination because of products derived from organisms.

As one of serum-free single media, KSOM medium is known (Proc Natl Acad Sci USA 2007; 104(36): 14289-14293 and Manipulating the Mouse Embryo, THIRD EDITION 2005; 149-193.). In embryos cultured in the KSOM medium, the number of cells in blastocysts is increased as compared to that in embryos cultured in a medium before the appearance of KSOM (Fertil Steril 2006; 86: 1252-1265.), however, the number does not reach to the number of cells in blastocysts developed in vivo (Biol Reprod 1994; 50: 1027-1033 and Reproduction 2009; 137: 271-283.).

It is known that amino acids act as biosynthetic precursors, energy sources, organic osmolytes, intracellular pH buffer substances, antioxidants, chelators and the like, and the addition of amino acids to media for embryo culture effectively acts on embryonic development (Semin Reprod Med 2000; 18(2): 205-218). The KSOM medium was a medium which contained only glutamine as an amino acid. It has been revealed, however, that a blastocyst development rate, a hatching rate and the number of cells in blastocysts are improved by adding 20 types of amino acids to the KSOM medium (Mol Reprod Dev 1995; 41(2): 232-238).

When developing a medium for culturing human pre-implantation embryos, researches using mouse embryos are recommended (Human Reproduction 1998; 13(4): 173-183 and Human Reproduction Update 2003; 9(6): 557-582). The KSOM medium or KSOMaa medium to which 20 types of amino acids are added has been researched using mouse embryos (Biol Reprod 1994; 50: 1027-1033 and Mol Reprod Dev 1995; 41(2): 232-238). It has been verified, however, that the media are suitable for culturing not only human embryos but also various animal embryos such as bovine, rabbit, rhesus monkey, swine and rat, and the media are now widely used.

DISCLOSURE OF INVENTION

Problems to be Solved by the Invention

The effect of each component in a culture medium depends on the concentrations of other components (Human Reproduction Update 2003; 9(6): 557-582), and thus a vast number of examinations are required in order to set concentrations suitable for embryonic development by individually combining 20 types of amino acids. Besides, in the research of embryos in the pre-implantation phase, such extensive analysis has been difficult due to scarcity of samples.

Because of this, most of the concentrations of amino acids added to an embryo culture medium such as KSOMaa medium are concentrations decided using the proliferation ability of somatic cells as an index and are not optimized for embryonic development.

The concentrations of amino acids added to the KSOMaa medium, for example, are just set to one-half of each specific concentration of 13 amino acids belonging to the essential amino acid group (Science 1959; 130, 432-437) and other 7 amino acids belonging to the non-essential amino acid group, which specific concentration has been decided using the auxotrophy of somatic cells as an index by Eagle and others. In addition, in a culture fluid G1 or G2 developed for human embryo culture, the concentrations decided using auxotrophy of somatic cells as an index by Eagle are directly used as the concentrations of amino acids added to the culture media.

Therefore, the development of culture media having the concentrations of amino acids suitable for in vitro embryo culture has been still demanded.

Means for Solving the Problems

In view of such demand, the present inventors repeated intensive research and consequently found the amino acid concentrations suitable for embryo culture.

By a mode of the present invention, there is provided a composition for embryo culture, which contains a constitution shown in Table A below.

TABLE A

| Component | mM |
| --- | --- |
| L-Alanine | 0.297 ± 0.089 |
| L-Asparagine | 0.015 ± 0.005 |
| L-Aspartic acid | 0.120 ± 0.036 |
| L-Glutamic acid | 0.550 ± 0.165 |
| Glycine | 0.979 ± 0.294 |
| L(−)-Proline | 0.105 ± 0.032 |
| L-Serine | 0.176 ± 0.053 |
| L(+)-Arginine | 0.108 ± 0.032 |
| L(−)-Cystine | 0.048 ± 0.014 |
| L-Histidine | 0.053 ± 0.016 |
| L(+)-Isoleucine | 0.036 ± 0.011 |
| L-Leucine | 0.081 ± 0.024 |
| L(+)-Lysine | 0.176 ± 0.053 |
| L-Methionine | 0.022 ± 0.007 |
| L(−)-Phenylalanine | 0.045 ± 0.013 |
| L(−)-Threonine | 0.109 ± 0.033 |
| L-Tryptophan | 0.018 ± 0.005 |
| L-Tyrosine | 0.048 ± 0.014 |
| L-Valine | 0.108 ± 0.032 |
| L-Glutamine or glutamine derivative | 0.398 ± 0.119 |
| Taurine | 1.412 ± 0.424 |

In an embodiment of the present invention, there is provided a composition for embryo culture, which further contains at least one component selected from the group consisting of electrolytes, organic acids, carbohydrates, pH indicators, pH adjusters, pH buffers, antibiotics, vitamins, trace metal elements, chelators, hormones, growth factors, lipids or constituents thereof, carrier proteins, extracellular matrix components, reducing substances and polymers in addition to the constitution shown in Table A above.

In an embodiment of the present invention, there is provided a composition for embryo culture, which contains the constitution shown in Table A above and electrolytes. In another embodiment of the present invention, there is provided a composition for embryo culture, which contains the constitution shown in Table A above, electrolytes, and organic acids and/or carbohydrates. In yet another embodiment of the present invention, there is also provided a composition for embryo culture, which contains the constitution shown in Table A above, electrolytes, and organic acids and/or carbohydrates, and further contains at least one component selected from the group consisting of pH indicators, pH adjusters, pH buffers, antibiotics, vitamins, trace metal elements, chelators, hormones, growth factors, lipids or constituents thereof, carrier proteins, extracellular matrix components, reducing substances and polymers.

MODE FOR CARRYING OUT THE INVENTION

As used herein, the term "composition for embryo culture" means a composition for treating gametes or embryos. In an embodiment of the present invention, using a composition for embryo culture, fertilized eggs or blastomeres can be cultured until blastocysts or until hatching of blastocysts. The term "can be cultured until blastocysts" contains, for example the culture of fertilized eggs or blastomeres until two to eight-cell embryos or morulae, but not limited thereto.

The composition for embryo culture involved in an embodiment of the present invention can be also used when sperm or egg cells are collected, matured, maintained or washed, or egg cells are fertilized in vitro. The composition for embryo culture involved in an embodiment of the present invention can be exchanged with a fresh composition for embryo culture involved in an embodiment of the present invention during embryo culture, but not limited thereto.

The "gamete" means a sperm or an ovum. In the present description, the "embryo" contains reconstructed embryos such as a fertilized egg, an early embryo and a nuclear transplant embryo, and contains embryos derived from mammals such as human, mouse, bovine, rabbit, rhesus monkey, swine and rat but not limited thereto. The "mammals" can be human, mouse, bovine, rabbit, rhesus monkey, swine or rat, but not limited thereto.

The blastocyst indicates an embryo after the cleavage stage in the early development of mammals. The blastocyst consists of an inner cell mass, a blastocoel and a trophectoderm surrounded by a zona pellucida. Hatching of blastocysts indicates a step of escape of embryos from the zona pellucida and is an essential process for reaching implantation of embryos.

It is known that in cultured embryos with abnormalities in the structure and physiological functions of embryos, hatching is delayed or hatching does not occur (Reprod Biomed Online 2003; 7: 228-234). Meanwhile, it is known that, for example, a blastocyst which hatches within a fixed period of time has a high implantation rate as compared to a blastocyst which does not hatch within a fixed period of time (Fertil Steril 2000; 74: 163-165).

It is known that the number of cells in blastocysts is positively correlated with a fetal development rate GT Reprod Fertil 1997; 109: 153-164) and positively correlated with a normal rate of chromosome (Hum Reprod; 2010: 1916-1926).

As methods for evaluating the quality of cultured embryos, there are a method for evaluating the morphological features of embryos using a microscope, such as a development speed, a blastocyst development rate and a hatching rate from a zona pellucida, an evaluation method by measuring the number of cells in blastocysts by nuclear staining, and the like.

Among these evaluation methods, the evaluation method based on hatching is one of the favorable evaluation methods for selecting cultured embryos with high quality. The number of cells in blastocysts is also one of the important evaluation methods for evaluating the quality of cultured embryos.

The amino, acids contained in a composition for embryo culture involved in an embodiment of the present invention can be in the free form or the form of a pharmaceutically acceptable salt. The amino acids contained in composition for embryo culture involved in another embodiment of the present invention can be also those which can be decomposed by hydrolysis and the like and converted into free amino acids. Such amino acids can be, for example, in the ester form, the N-acyl form, an oligopeptide and the like.

Glutamine, for example, can be a glutamine derivative such as glycyl-L-glutamine, L-alanyl-L-glutamine, L-leucyl-L-glutamine, L-valyl-L-glutamine or L-isoleucyl-L-glutamine. These glutamine derivatives can be used alone or two or more glutamine derivatives can be used in combination. In an embodiment of the present invention, the glutamine derivative is, for example, glycyl-L-glutamine or L-alanyl-L-glutamine. In another embodiment of the present invention, the glutamine derivative is glycyl-L-glutamine. In another embodiment of the present invention, the glutamine derivative is L-alanyl-L-glutamine.

In addition, for example, in cysteine, a portion or all thereof can be cysteine.

In an embodiment of the present invention, taurine contained in a composition for embryo culture can be in the free form or the form of a pharmaceutically acceptable salt. In another embodiment of the present invention, taurine contained in a composition for embryo culture can be that which can be converted into taurine by dehydrogenation and the like. Such taurine, for example, can be hypotaurine.

The composition for embryo culture involved in an embodiment of the present invention can contain at least one component selected from the group consisting of electrolytes, organic acids, carbohydrates, pH indicators, pH adjusters, pH buffers, antibiotics, vitamins, trace metal elements, chelators, hormones, growth factors, lipids or constituents thereof, carrier proteins, extracellular matrix components, reducing substances and polymers and the like, as needed.

The electrolytes are not limited, and include sodium chloride, potassium chloride, sodium dihydrogen phosphate, calcium chloride dihydrate, magnesium sulfate heptahydrate, sodium hydrogen carbonate, calcium chloride, calcium gluconate, magnesium chloride, magnesium sulfate and dipotassium hydrogen phosphate and the like. These electrolytes can be used alone or two or more electrolytes can be used in combination.

The organic acids are not limited, and include pyruvic acid, acetic acid, citric acid, succinic acid, malic acid, α-ketoglutaric acid, fumaric acid, oxaloacetic acid, isocitric acid, oxalosuccinic acid, tartaric acid, adipic acid, lactic acid and salts thereof. These organic acids can be used alone or two or more organic acids can be used in combination.

The carbohydrates are not limited, and include glucose, maltose, fructose, xylitol, sorbitol and trehalose and the like. These carbohydrates can be used alone or two or more carbohydrates can be used in combination.

The pH indicators are not limited, and include phenol red and the like.

The pH adjusters are not limited, and include hydrochloric acid, acetic acid, sodium hydroxide and the like.

The pH buffers are not limited, and include HEPES (N-2-hydroxyethylpiperazine-N'-2-ethanesulfonic acid), MOPS (3-morpholinopropane sulfonic acid), tris[hydroxymethyl]aminomethane, N-tris[hydroxymethyl]methyl-2-aminoethanesulfonic acid and the like. These pH buffers can be used alone or two or more pH buffers can be used in combination.

The antibiotics are not limited, and include penicillin, streptomycin, kanamycin, gentamicin, erythromycin, amphotericin B, nystatin and the like. These antibiotics can be used alone or two or more antibiotics can be used in combination.

The vitamins are not limited, and include vitamin A, vitamin B group, vitamin C, vitamin C group, vitamin E, nicotinic acid, biotin, folic acid and the like. These vitamins can be used alone or two or more vitamins can be used in combination.

The trace metal elements are not limited, and include zinc, iron, manganese, copper, iodine, selenium and cobalt. These trace metal elements are not limited, and can be used in the free form or can be used as pharmaceutically acceptable compounds containing these trace metal elements. These trace metal elements can be used alone or two or more trace metal elements can be used in combination.

The chelators are not limited, and include EGTA (ethyleneglycol bis tetraacetic acid), EDTA (ethylene diamine tetraacetic acid), EDDA (ethylene diamine diacetic acid) and DTPA (diethylene triamine pentaacetic acid) and the like. These chelators can be used alone or two more chelators can be used in combination.

The hormones are not limited, and include insulin, hydrocortisone, dexamethasone, triiodothyronine, gonadotropin, estrogen, progesterone and the like. These hormones can be used alone or two or more hormones can be used in combination.

The growth factors are not limited, and include epidermal growth factor, fibroblast growth factors, platelet-derived growth factors, insulin-like growth factors, growth hormone and the like. These growth factors can be used alone or two or more growth factors can be used in combination.

The lipids or constituents thereof are not limited, and include fatty acids such as oleic acid, linoleic acid, linolenic acid, arachidonic acid, palmitic acid, oleic acid, palmitoleic acid, stearic acid, myristic acid, and salts thereof, or cholesterol, ethanolamine, choline, sphingomyelin, cardiolipin and the like. These lipids or constituents thereof can be used alone or two or more thereof can be used in combination.

The carrier proteins are not limited, and include albumin, transferrin, ceruloplasmin and the like. These carrier proteins can be used alone or two or more carrier proteins can be used in combination. Albumin is not limited, and can be bovine serum albumin, human serum albumin, recombinant bovine serum albumin or recombinant human serum albumin, or a mixture thereof.

The extracellular matrix components are not limited, and include fibronectin, collagen, gelatin, hyaluronan and the like. These extracellular matrix components can be used alone or two or more extracellular matrix components can be used in combination.

The reducing substances are not limited, and include 2-mercaptoethanol, dithiothreitol, reduced glutathione and the like. These reducing substances can be used alone or two or more reducing substances can be used in combination.

The polymers are not limited, and include PVP (polyvinyl pyrrolidone), PVA (polyvinyl alcohol), dextran and the like. These polymers can be used alone or two or more polymers can be used in combination.

The composition for embryo culture involved in an embodiment of the present invention can be produced by combining constituents by conventional method. A composition for embryo culture, for example, can be produced or supplied in the form of a sterile solution, the form of a dilution type sterile concentrated solution, or the form of a dissolution type sterile lyophilized product by a conventional method.

Therefore, the composition for embryo culture involved in an embodiment of the present invention can be in the form of a sterile solution, the form of a sterile concentrated solution, or the form of a sterile lyophilized product. When the composition for embryo culture involved in an embodiment of the present invention is in the form of a sterile concentrated solution or the form of a sterile lyophilized product as described above, by diluting or dissolving the composition with sterile water before use, a composition for embryo culture in the form of a sterile solution can be obtained, but not limited thereto.

EXAMPLES

Example 1

Medium Constitution

Table 2 shows, in the constitution of the KSOMaa medium (Comparative Example 1) as a control and the constitution of the medium in Example 1, component names contained in the media, molecular weights (M.W.) and contents thereof from the left column.

TABLE 2

| Component Name | M.W. | Comparative Example 1 mM | Comparative Example 1 g/L | Example 1 mM | Example 1 g/L |
| --- | --- | --- | --- | --- | --- |
| L-Alanine | 89.09 | 0.050 | 0.004 | 0.297 | 0.026 |
| L-Asparagine monohydrate | 150.13 | 0.050 | 0.008 | 0.015 | 0.002 |
| L-Aspartic acid | 133.10 | 0.050 | 0.007 | 0.120 | 0.016 |
| L-Glutamic acid | 147.13 | 0.050 | 0.007 | 0.550 | 0.081 |
| Glycine | 75.07 | 0.050 | 0.004 | 0.979 | 0.073 |
| L(−)-Proline | 115.13 | 0.050 | 0.006 | 0.105 | 0.012 |
| L-Serine | 105.09 | 0.050 | 0.005 | 0.176 | 0.018 |
| L(+)-Arginine hydrochloride | 210.66 | 0.300 | 0.063 | 0.108 | 0.023 |
| L(−)-Cystine | 240.30 | 0.050 | 0.012 | 0.048 | 0.012 |
| L-Histidine hydrochloride monohydrate | 209.63 | 0.100 | 0.021 | 0.053 | 0.011 |
| L(+)-Isoleucine | 131.17 | 0.200 | 0.026 | 0.036 | 0.005 |
| L-Leucine | 131.17 | 0.200 | 0.026 | 0.081 | 0.011 |
| L(+)-Lysine hydrochloride | 182.65 | 0.200 | 0.037 | 0.176 | 0.032 |
| L-Methionine | 149.21 | 0.050 | 0.007 | 0.022 | 0.003 |
| L(−)-Phenylalanine | 165.19 | 0.100 | 0.017 | 0.045 | 0.007 |
| L(−)-Threonine | 119.12 | 0.200 | 0.024 | 0.109 | 0.013 |
| L-Tryptophan | 204.23 | 0.025 | 0.005 | 0.018 | 0.004 |
| L-Tyrosine | 181.19 | 0.100 | 0.018 | 0.048 | 0.009 |
| L-Valine | 117.15 | 0.200 | 0.023 | 0.108 | 0.013 |
| Glycyl-L-glutamine monohydrate | 221.21 | 1.000 | 0.221 | 0.398 | 0.088 |
| Taurine | 125.15 | — | — | 1.412 | 0.177 |
| Sodium chloride | 58.44 | 95.000 | 5.552 | 114.718 | 6.704 |
| Potassium chloride | 74.55 | 2.500 | 0.186 | 5.200 | 0.388 |
| Potassium dihydrogen phosphate | 136.09 | 0.350 | 0.048 | 0.300 | 0.041 |
| Calcium chloride dihydrate | 147.01 | 1.710 | 0.251 | 1.117 | 0.164 |
| Magnesium sulfate heptahydrate | 246.48 | 0.200 | 0.049 | 0.467 | 0.115 |
| Sodium hydrogen | 84.01 | 25.000 | 2.100 | 25.000 | 2.100 |

TABLE 2-continued

| Component Name | M.W. | Comparative Example 1 mM | Comparative Example 1 g/L | Example 1 mM | Example 1 g/L |
|---|---|---|---|---|---|
| carbonate | | | | | |
| D-Glucose | 180.16 | 0.200 | 0.036 | 2.998 | 0.540 |
| Sodium pyruvate | 110.04 | 0.200 | 0.022 | 0.183 | 0.020 |
| Sodium L-lactate | 112.06 | 10.000 | 2.186 | 4.540 | 0.992 |
| Trisodium citrate dihydrate | 294.10 | — | — | 0.127 | 0.037 |
| EDTA•2Na | 372.24 | 0.010 | 0.004 | — | — |
| Phenol red | 354.38 | 0.003 | 0.001 | 0.003 | 0.001 |
| Gentamicin sulfate | — | — | 0.010 | — | 0.010 |

Collection of Sperm

After sacrificing ICR male mice (Japan SLC, Inc.), the cauda epididymis was cut out. A sperm mass obtained by incising the epididymal duct in the middle of the cauda epididymis was collected in 300 μL of TYH medium supplemented with 0.4% bovine serum albumin prepared under mineral oil. The collected sperm mass was precultured under conditions of 37° C. and 6% $CO_2$ for an hour.

Collection of Ova

To ICR female mice (Japan SLC, Inc.), 7.5 international unit of PMSG (pregnant mare serum gonadotropin, ASKA Pharmaceutical Co., Ltd., SEROTROPIN (Trade Mark)) was intraperitoneally administered. After 48 hours, 7.5 international unit of hCG (human chorionic gonadotropin, ASKA Pharmaceutical Co., Ltd., GONATROPIN (Trade Mark)) was intraperitoneally administered to induce superovulation, and such mice were sacrificed at 15 hours after administration of hCG. A uterine tube was cut out immediately after sacrificing. From the ampulla of the uterine tube, cumulus oocyte complexes were collected in 300 μL of TYH medium supplemented with 0.4% bovine serum albumin prepared with mineral oil. The collected cumulus oocyte complexes were cultured under conditions of 37° C. and 6% $CO_2$ until in vitro fertilization.

In Vitro Fertilization

To the TYH medium containing the collected cumulus oocyte complexes, the precultured sperm were added so as to be 150 sperm/μL. After in vitro fertilization under conditions of 37° C. and 6% $CO_2$ for 6 hours, an ovum in which the second polar body and two pronuclei could be observed was decided as a fertilized egg and was directly used for the following experiment.

Embryo Culture Test

Using the medium in Example 1 and the medium in Comparative Example 1, a 100 μL drop of each medium supplemented with 0.1% bovine serum albumin was prepared in a culture dish with a diameter of 60 mm under mineral oil, and was left to stand under conditions of 37° C., 5% $O_2$ and 6% $CO_2$ overnight for equilibration.

To the drop of each medium after equilibration, a fertilized egg was transferred. The fertilized egg was washed by moving into several drops. The washed fertilized egg was transferred to a fresh drop of each medium and cultured under conditions of 37° C., 5% $O_2$ and 6% $CO_2$ for 4 days. The embryo on the 4th day of culture was observed with a microscope and the percentage of embryos reaching from fertilized eggs to blastocysts or the hatching stage was calculated. The obtained results are shown in Table 3.

TABLE 3

| Medium | Number of cultured fertilized eggs (Repetition frequency) | Blastocyst development rate (%) Total | Blastocyst development rate (%) Hatching |
|---|---|---|---|
| Comparative Example 1 | 104 (6) | 95.8 ± 2.2 | 72.8 ± 3.0 |
| Example 1 | 104 (6) | 98.1 ± 1.3 | 87.8 ± 2.9* |

Mean value ± Standard error
*Significant difference compared with the medium in Comparative Example 1 (p = 0.0065, Wilcoxon test)

The blastocysts obtained on the 4th day of culture were fluorescently stained using DAPI (4',6-Diamidine-2'-phenylindole dihydrochloride) (Roche Diagnostics K.K.) and the number of cells in the blastocysts was measured. The obtained results are shown in Table 4.

TABLE 4

| Medium | Number of analyzed blastocysts | Total number of cells |
|---|---|---|
| Comparative Example 1 | 98 | 80.2 ± 1.5 |
| Example 1 | 94 | 90.2 ± 2.0** |

Mean value ± Standard error
**Significant difference compared with the medium in Comparative Example 1 (p = 0.0003, Wilcoxon test)

As shown in Table 3 and Table 4, in the group cultured in the medium in Example 1, the hatching rate was significantly improved and the number of cells in blastocysts was significantly increased as compared to those in the group cultured in the medium in Comparative Example 1. This result shows that the medium in Example 1 involved in an embodiment of the present invention is more excellent in terms of being capable of causing the stimulatory action and quality improvement on embryonic development than the medium in Comparative Example 1.

Example 2

A medium (Example 2) was prepared by replacing the constitution of amino acids contained in the medium in Comparative Example 1 shown in Table 2 above with the constitution of amino acids including taurine contained in the medium in Example 1 shown in Table 2 (Table 5).

TABLE 5

| Component Name | M.W. | Comparative Example 1 mM | Comparative Example 1 g/L | Example 2 mM | Example 2 g/L |
|---|---|---|---|---|---|
| L-Alanine | 89.09 | 0.050 | 0.004 | 0.297 | 0.026 |
| L-Asparagine monohydrate | 150.13 | 0.050 | 0.008 | 0.015 | 0.002 |
| L-Aspartic acid | 133.10 | 0.050 | 0.007 | 0.120 | 0.016 |
| L-Glutamic acid | 147.13 | 0.050 | 0.007 | 0.550 | 0.081 |
| Glycine | 75.07 | 0.050 | 0.004 | 0.979 | 0.073 |
| L(−)-Proline | 115.13 | 0.050 | 0.006 | 0.105 | 0.012 |
| L-Serine | 105.09 | 0.050 | 0.005 | 0.176 | 0.018 |
| L(+)-Arginine hydrochloride | 210.66 | 0.300 | 0.063 | 0.108 | 0.023 |
| L(−)-Cystine | 240.30 | 0.050 | 0.012 | 0.048 | 0.012 |
| L-Histidine hydrochloride monohydrate | 209.63 | 0.100 | 0.021 | 0.053 | 0.011 |
| L(+)-Isoleucine | 131.17 | 0.200 | 0.026 | 0.036 | 0.005 |
| L-Leucine | 131.17 | 0.200 | 0.026 | 0.081 | 0.011 |
| L(+)-Lysine | 182.65 | 0.200 | 0.037 | 0.176 | 0.032 |

TABLE 5-continued

| Component Name | M.W. | Comparative Example 1 mM | Comparative Example 1 g/L | Example 2 mM | Example 2 g/L |
|---|---|---|---|---|---|
| hydrochloride | | | | | |
| L-Methionine | 149.21 | 0.050 | 0.007 | 0.022 | 0.003 |
| L(−)-Phenylalanine | 165.19 | 0.100 | 0.017 | 0.045 | 0.007 |
| L(−)-Threonine | 119.12 | 0.200 | 0.024 | 0.109 | 0.013 |
| L-Tryptophan | 204.23 | 0.025 | 0.005 | 0.018 | 0.004 |
| L-Tyrosine | 181.19 | 0.100 | 0.018 | 0.048 | 0.009 |
| L-Valine | 117.15 | 0.200 | 0.023 | 0.108 | 0.013 |
| Glycyl-L-glutamine monohydrate | 221.21 | 1.000 | 0.221 | 0.398 | 0.088 |
| Taurine | 125.15 | — | — | 1.412 | 0.177 |
| Sodium chloride | 58.44 | 95.000 | 5.552 | 95.000 | 5.552 |
| Potassium chloride | 74.55 | 2.500 | 0.186 | 2.500 | 0.186 |
| Potassium dihydrogen phosphate | 136.09 | 0.350 | 0.048 | 0.350 | 0.048 |
| Calcium chloride dihydrate | 147.01 | 1.710 | 0.251 | 1.710 | 0.251 |
| Magnesium sulfate heptahydrate | 246.48 | 0.200 | 0.049 | 0.200 | 0.049 |
| Sodium hydrogen carbonate | 84.01 | 25.000 | 2.100 | 25.000 | 2.100 |
| D-Glucose | 180.16 | 0.200 | 0.036 | 0.200 | 0.036 |
| Sodium pyruvate | 110.04 | 0.200 | 0.022 | 0.200 | 0.022 |
| Sodium L-lactate | 112.06 | 10.000 | 2.186 | 10.000 | 2.186 |
| Trisodium citrate dihydrate | 294.10 | — | — | — | — |
| EDTA•2Na | 372.24 | 0.010 | 0.004 | 0.010 | 0.004 |
| Phenol red | 354.38 | 0.003 | 0.001 | 0.003 | 0.001 |
| Gentamicin sulfate | — | — | 0.010 | — | 0.010 |

Using the medium in Comparative Example 1 and the medium in Example 2, the embryo culture test was carried out in the same condition as in the embryo culture test described in Example 1. The obtained results are shown in Table 6.

TABLE 6

| Medium | Number of analyzed blastocysts | Total number of cells |
|---|---|---|
| Comparative Example 1 | 131 | 86.2 ± 1.4 |
| Example 2 | 131 | 90.2 ± 1.6* |

Mean value ± Standard error
*Significant difference compared with the medium in Comparative Example 1 ($p = 0.0467$, Wilcoxon test)

As shown in Table 6, in the group cultured in the medium in Example 2 involved in an embodiment of the present invention, the number of cells in blastocysts was significantly increased as compared to that in the group cultured in Comparative Example 1. As described above, the constitution of amino acids including taurine contained in a composition for embryo culture involved in an embodiment of the present invention has action to stimulate the development of embryos regardless of medium constitutions other than the above constitution.

Examples 3 and 4

A medium having a constitution with 0.7 times the concentration of the constitution of amino acids including taurine contained in the medium in Example 1 shown in Table 2 (Example 3) and a medium having a constitution with 1.3 times the concentration thereof (Example 4) were prepared (Table 7).

TABLE 7

| | Example 1 mM | Example 3 mM | Example 4 mM |
|---|---|---|---|
| L-Alanine | 0.297 | 0.208 | 0.386 |
| L-Asparagine monohydrate | 0.015 | 0.011 | 0.020 |
| L-Aspartic acid | 0.120 | 0.084 | 0.156 |
| L-Glutamic acid | 0.550 | 0.385 | 0.715 |
| Glycine | 0.979 | 0.685 | 1.273 |
| L(−)-Proline | 0.105 | 0.074 | 0.137 |
| L-Serine | 0.176 | 0.123 | 0.229 |
| L(+)-Arginine hydrochloride | 0.108 | 0.076 | 0.140 |
| L(−)-Cystine | 0.048 | 0.034 | 0.062 |
| L-Histidine hydrochloride monohydrate | 0.053 | 0.037 | 0.069 |
| L(+)-Isoleucine | 0.036 | 0.025 | 0.047 |
| L-Leucine | 0.081 | 0.057 | 0.105 |
| L(+)-Lysine hydrochloride | 0.176 | 0.123 | 0.229 |
| L-Methionine | 0.022 | 0.015 | 0.029 |
| L(−)-Phenylalanine | 0.045 | 0.032 | 0.059 |
| L(−)-Threonine | 0.109 | 0.076 | 0.142 |
| L-Tryptophan | 0.018 | 0.013 | 0.023 |
| L-Tyrosine | 0.048 | 0.034 | 0.062 |
| L-Valine | 0.108 | 0.076 | 0.140 |
| Glycyl-L-glutamine monohydrate | 0.398 | 0.279 | 0.517 |
| Taurine | 1.412 | 0.988 | 1.836 |
| Sodium chloride | 114.718 | 114.718 | 114.718 |
| Potassium chloride | 5.200 | 5.200 | 5.200 |
| Potassium dihydrogen phosphate | 0.300 | 0.300 | 0.300 |
| Calcium chloride dihydrate | 1.117 | 1.117 | 1.117 |
| Magnesium sulfate heptahydrate | 0.467 | 0.467 | 0.467 |
| Sodium hydrogen carbonate | 25.000 | 25.000 | 25.000 |
| D-Glucose | 2.998 | 2.998 | 2.998 |
| Sodium pyruvate | 0.183 | 0.183 | 0.183 |
| Sodium L-lactate | 4.540 | 4.540 | 4.540 |
| Trisodium citrate dihydrate | 0.127 | 0.127 | 0.127 |
| EDTA•2Na | — | — | — |
| Phenol red | 0.003 | 0.003 | 0.003 |
| Gentamicin sulfate | 0.010 (g/L) | 0.010 (g/L) | 0.010 (g/L) |

In Table 7, the unit of concentration of each component is mM, unless otherwise described.

Using the medium in Example 1, the medium in Example 3 and the medium in Example 4, the embryo culture test was carried out in the same condition as in the embryo culture test described in Example 1. The obtained results are shown in Table 8 and Table 9.

TABLE 8

| | Number of cultured fertilized eggs | Blastocyst development rate (%) | |
|---|---|---|---|
| Medium | (Repetition frequency) | Total | Hatching |
| Example 1 | 150 (15) | 92.7 ± 3.0 | 72.7 ± 3.6 |
| Example 3 | 150 (15) | 94.0 ± 2.4 | 74.7 ± 4.1 |
| Example 4 | 150 (15) | 94.0 ± 2.4 | 72.0 ± 3.9 |

Mean value ± Standard error
No significant differences between groups (Steel-Dwass test)

TABLE 9

| Medium | Number of analyzed blastocysts | Total number of cells |
|---|---|---|
| Example 1 | 124 | 102.1 ± 2.0 |
| Example 3 | 142 | 99.4 ± 1.4 |
| Example 4 | 137 | 101.4 ± 1.6 |

Mean value ± Standard error
No significant differences between groups (Steel-Dwass test)

As shown in Table 8 and Table 9, even by the medium having the constitution with 0.7 times the concentration of the constitution of amino acids including taurine contained in the medium in Example 1 (Example 3) and the medium having the constitution with 1.3 times the concentration thereof (Example 4), significant differences in validity were not observed. This reveals that the validity of the constitution of amino acids including taurine contained in the medium in Example 1, which is the composition for embryo culture involved in the present embodiment, is not lost within a concentration range of at least 0.7 to 1.3-times.

Example 5

Human Embryo Culture Test

Table 10 shows, in the constitution of a medium in Example 5, component names contained in the medium, molecular weights (M.W.) and contents thereof from the left column.

TABLE 10

| | | Example 5 | |
|---|---|---|---|
| Component Name | M.W. | mM | g/L |
| L-Alanine | 89.09 | 0.297 | 0.026 |
| L-Asparagine monohydrate | 150.13 | 0.015 | 0.002 |
| L-Aspartic acid | 133.10 | 0.120 | 0.016 |
| L-Glutamic acid | 147.13 | 0.550 | 0.081 |
| Glycine | 75.07 | 0.979 | 0.073 |
| L(−)-Proline | 115.13 | 0.105 | 0.012 |
| L-Serine | 105.09 | 0.176 | 0.018 |
| L(+)-Arginine hydrochloride | 210.66 | 0.108 | 0.023 |
| L(−)-Cystine | 240.30 | 0.048 | 0.012 |
| L-Histidine hydrochloride monohydrate | 209.63 | 0.053 | 0.011 |
| L(+)-Isoleucine | 131.17 | 0.036 | 0.005 |
| L-Leucine | 131.17 | 0.081 | 0.011 |
| L(+)-Lysine hydrochloride | 182.65 | 0.176 | 0.032 |
| L-Methionine | 149.21 | 0.022 | 0.003 |
| L(−)-Phenylalanine | 165.19 | 0.045 | 0.007 |
| L(−)-Threonine | 119.12 | 0.109 | 0.013 |
| L-Tryptophan | 204.23 | 0.018 | 0.004 |
| L-Tyrosine | 181.19 | 0.048 | 0.009 |
| L-Valine | 117.15 | 0.108 | 0.013 |
| Glycyl-L-glutamine monohydrate | 221.21 | 0.398 | 0.088 |
| Taurine | 125.15 | 1.412 | 0.177 |
| Sodium chloride | 58.44 | 114.718 | 6.704 |
| Potassium chloride | 74.55 | 5.200 | 0.388 |
| Potassium dihydrogen phosphate | 136.09 | 0.300 | 0.041 |
| Calcium chloride dihydrate | 147.01 | 1.117 | 0.164 |
| Magnesium sulfate heptahydrate | 246.48 | 0.467 | 0.115 |
| Sodium hydrogen carbonate | 84.01 | 25.000 | 2.100 |
| D-Glucose | 180.16 | 2.998 | 0.540 |

TABLE 10-continued

| | | Example 5 | |
|---|---|---|---|
| Component Name | M.W. | mM | g/L |
| Sodium pyruvate | 110.04 | 0.183 | 0.020 |
| Sodium L-lactate | 112.06 | 4.540 | 0.992 |
| Trisodium citrate dihydrate | 294.10 | 0.127 | 0.037 |
| EDTA•2Na | 372.24 | 0.010 | 0.004 |
| Phenol red | 354.38 | 0.003 | 0.001 |
| Gentamicin sulfate | — | — | 0.010 |

A 20 µL drop of the medium in Example 5 to which 0.05% recombinant human albumin was added was prepared in a culture dish with a diameter of 35 mm under mineral oil and was left to stand under conditions of 37° C., 4% $O_2$ and 6% $CO_2$ overnight for equilibration.

As human fertilized eggs, fertilized eggs after freezing and thawing were used, which were not intended to be used for treatment after this and were agreed on the research use. Each one of human fertilized eggs after freeze-thawing was transferred to each medium after equilibration. After that, the human fertilized egg was washed by moving into several drops. The washed fertilized egg was transferred to a fresh drop of each medium and cultured under conditions of 37° C., 4% $O_2$ and 6% $CO_2$ for 5 to 6 days. The embryo was observed with a microscope every day from the second day after the onset of culture and the developmental stage of the embryo was observed. The obtained typical results are shown in Table 11.

TABLE 11

| Embryo medium | No. | Developmental stage | | | |
|---|---|---|---|---|---|
| | | Day 2 | Day 3 | Day 4 | Day 5-6 |
| Example 5 | 1 | 4 cell stage | 8 cell stage | Morula stage | Blastocyst stage |
| | 2 | 4 cell stage | 6 cell stage | 8 cell stage | Morula stage |
| | 3 | 2 cell stage | 6 cell stage | 9 cell stage | Blastocyst stage |
| | 4 | 2 cell stage | 4 cell stage | 5 cell stage | Morula stage |

As shown in Table 11, it is clear that the medium in Example 5 according to an embodiment of the present invention is an excellent culture medium for human embryos.

The invention claimed is:
1. A composition for an embryo culture, comprising:
a mixture of the components shown in Table A below, the components being present in the concentrations shown in Table A below; and
a chelator,

TABLE A

| Components | mM |
|---|---|
| L-Alanine | 0.297 ± 0.089 |
| L-Asparagine | 0.015 ± 0.005 |
| L-Aspartic acid | 0.120 ± 0.036 |
| L-Glutamic acid | 0.550 ± 0.165 |
| Glycine | 0.979 ± 0.294 |
| L(−)-Proline | 0.105 ± 0.032 |
| L-Serine | 0.176 ± 0.053 |
| L(+)-Arginine | 0.108 ± 0.032 |
| L(−)-Cystine | 0.048 ± 0.014 |
| L-Histidine | 0.053 ± 0.016 |

TABLE A-continued

| Components | mM |
|---|---|
| L(+)-Isoleucine | 0.036 ± 0.011 |
| L-Leucine | 0.081 ± 0.024 |
| L(+)-Lysine | 0.176 ± 0.053 |
| L-Methionine | 0.022 ± 0.007 |
| L(−)-Phenylalanine | 0.045 ± 0.013 |
| L(−)-Threonine | 0.109 ± 0.033 |
| L-Tryptophan | 0.018 ± 0.005 |
| L-Tyrosine | 0.048 ± 0.014 |
| L-Valine | 0.108 ± 0.032 |
| L-Glutamine or glutamine derivative | 0.398 ± 0.119 |
| Taurine | 1.412 ± 0.424. |

2. The composition for an embryo culture according to claim 1, further comprising electrolytes.

3. The composition for an embryo culture according to claim 2, further comprising organic acids and/or carbohydrates.

4. The composition for an embryo culture according to claim 3, further comprising at least one component selected from the group consisting of pH indicators, pH adjusters, pH buffers, antibiotics, vitamins, trace metal elements, hormones, growth factors, lipids or constituents thereof, carrier proteins, extracellular matrix components, reducing substances and polymers.

5. The composition for an embryo culture according to claim 1, wherein the glutamine derivative is glycyl-L-glutamine, L-alanyl-L-glutamine, L-leucyl-L-glutamine, L-valyl-L-glutamine or L-isoleucyl-L-glutamine.

6. The composition for an embryo culture according to claim 1, wherein the chelator is at least one selected from the group consisting of ethyleneglycol bis tetraacetic acid, ethylene diamine tetraacetic acid, ethylene diamine diacetic acid and diethylene triamine pentaacetic acid.

7. The composition for an embryo culture according to claim 1, wherein the composition is in the form of a sterile solution, a sterile concentrated solution or a sterile lyophilized product.

* * * * *